(12) United States Patent
Murata et al.

(10) Patent No.: US 9,273,151 B2
(45) Date of Patent: Mar. 1, 2016

(54) PROTEINACEOUS-SUBSTANCE-BINDING LOW-MOLECULAR-WEIGHT COMPOUND

(75) Inventors: Dai Murata, Hyogo (JP); Shinichi Yoshida, Hyogo (JP)

(73) Assignee: Kaneka Corporation, Osaka (JP)

( * ) Notice: Subject to any disclaimer, the term of this patent is extended or adjusted under 35 U.S.C. 154(b) by 53 days.

(21) Appl. No.: 14/007,000

(22) PCT Filed: Mar. 23, 2012

(86) PCT No.: PCT/JP2012/057521
§ 371 (c)(1),
(2), (4) Date: Sep. 24, 2013

(87) PCT Pub. No.: WO2012/128353
PCT Pub. Date: Sep. 27, 2012

(65) Prior Publication Data
US 2014/0018524 A1    Jan. 16, 2014

(30) Foreign Application Priority Data
Mar. 24, 2011 (JP) .................. 2011-066589

(51) Int. Cl.
| C07K 1/14 | (2006.01) |
| C07K 17/00 | (2006.01) |
| C07K 1/22 | (2006.01) |
| B01J 20/289 | (2006.01) |
| B01J 20/32 | (2006.01) |
| B01D 15/38 | (2006.01) |

(52) U.S. Cl.
CPC ............ *C07K 17/00* (2013.01); *B01D 15/3809* (2013.01); *B01J 20/289* (2013.01); *B01J 20/3202* (2013.01); *B01J 20/3219* (2013.01); *B01J 20/3246* (2013.01); *C07K 1/22* (2013.01)

(58) Field of Classification Search
None
See application file for complete search history.

(56) References Cited

U.S. PATENT DOCUMENTS

| 4,696,980 | A | 9/1987 | Porath |
| 5,502,022 | A | 3/1996 | Schwarz et al. |
| 5,719,269 | A | 2/1998 | Schwarz et al. |
| 6,117,996 | A | 9/2000 | Lowe et al. |
| 6,399,750 | B1 | 6/2002 | Johansson |
| 6,610,630 | B2 | 8/2003 | Schwarz et al. |
| 6,831,161 | B1 | 12/2004 | Uhlen et al. |
| 7,709,209 | B2 | 5/2010 | Hober et al. |
| 7,834,158 | B2 | 11/2010 | Hober |
| 8,076,477 | B2 | 12/2011 | Betley et al. |
| 8,198,404 | B2 | 6/2012 | Hober |
| 8,354,510 | B2 | 1/2013 | Hober et al. |
| 2001/0014649 | A1 | 8/2001 | Schwarz et al. |
| 2005/0100970 | A1 | 5/2005 | Uhlen et al. |
| 2005/0143566 | A1 | 6/2005 | Hober |
| 2006/0194950 | A1 | 8/2006 | Hober et al. |
| 2006/0194955 | A1 | 8/2006 | Hober et al. |
| 2006/0257972 | A1 | 11/2006 | Ishihara |
| 2009/0221801 | A1* | 9/2009 | Betley et al. ............... 530/387.1 |
| 2010/0022760 | A1 | 1/2010 | Hober et al. |
| 2010/0286373 | A1 | 11/2010 | Majima et al. |
| 2011/0112276 | A1 | 5/2011 | Hober |
| 2012/0238724 | A1 | 9/2012 | Hober |
| 2013/0184438 | A1 | 7/2013 | Hober et al. |

FOREIGN PATENT DOCUMENTS

| EP | 1123389 A1 | 8/2001 |
| JP | S615100 A | 1/1986 |
| JP | H10500615 A | 1/1998 |
| JP | H11512442 A | 10/1999 |
| JP | 2000-500649 A | 1/2000 |
| JP | 2002-527107 A | 8/2002 |
| JP | 2005-538693 A | 12/2005 |
| JP | 3844496 B2 | 11/2006 |
| JP | 2007-252368 A | 10/2007 |
| JP | 2009-531653 A | 9/2009 |
| JP | 2009-244252 A | 10/2009 |
| WO | WO-03080655 A1 | 10/2003 |
| WO | WO-2004/087761 A1 | 10/2004 |
| WO | WO-2009/113637 A1 | 9/2009 |
| WO | WO-2009/141384 A2 | 11/2009 |

OTHER PUBLICATIONS

Justine R. A., Cottam and Peter J. Steel, Synthesis of a family of heterocyclic ligands derived from bisphenols: new flexible bridging ligands for use in metallosupramolecular chemistry, Tetrahedron, 2008, vol. 64, No. 13, p. 2915-2923.

L. Guerrier, et al., New method for the selective capture of antibodies under phsiological conditions, Bioseparation, 2000, vol. 9, No. 4, p. 211-221.

Ana C. A. Roque et al., Affinity-based methodologies and ligands for antibody purification: Advances and perspectives, Journal of Chromatography A, vol. 1160, No. 1-2, 2007, p. 44-55.

Duncan Low et al., Future of antibody purification, Journal of Chromatography B, 2007, vol. 848, No. 1, p. 48-63.

International Search Report issued in PCT/JP2012/057521, mailing date Jul. 3, 2012, with English translation of International Search Report.

Extended European Search Report issued Mar. 24, 2015 in Appl. No. EP12760318.1.

* cited by examiner

*Primary Examiner* — Marcela M Cordero Garcia
*Assistant Examiner* — Mindy Newman
(74) *Attorney, Agent, or Firm* — Novak Druce Connolly Bove + Quigg LLP

(57) ABSTRACT

The low-molecular-weight compound represented by the general formula (1): ArX-(Linker)-ArYHB (1), wherein ArX is a structure containing an optionally substituted aromatic six-membered ring, ArYHB is a structure containing an optionally substituted aromatic six-membered ring having a proton donor, the atom group "Linker" has not less than 4 and not more than 30 atoms and binds ArX with ArYHB, is used for binding a proteinaceous substance.

20 Claims, 2 Drawing Sheets

(A) Binding curves with respect to the low-molecular-weight compounds (2) to (5)

(B) Binding curves with respect to the low-molecular-weight compounds (6) to (9)

(C) Binding curves with respect to the low-molecular-weight compounds (10) to (13)

(D) Binding curves with respect to the low-molecular-weight compounds (14) to (17)

PROTEINACEOUS-SUBSTANCE-BINDING LOW-MOLECULAR-WEIGHT COMPOUND

CROSS-REFERENCE TO RELATED APPLICATIONS

This Application is a National Stage of PCT International Application No. PCT/JP2012/057521, filed on Mar. 23, 2012, and claims priority of Japanese Patent Application No. 2011-066589, filed on Mar. 24, 2011. The disclosures of the aforementioned applications are incorporated herein in their entirety by reference.

TECHNICAL FIELD

The present invention relates to a method for separating, purifying, characterizing, identifying or quantitating a proteinaceous substrate by utilizing a low-molecular-weight compound which specifically binds to an antibody.

BACKGROUND ART

In recent years, demand of a biological polymer, such as a protein, an enzyme and a nucleic acid, has been drastically increased for biopharmaceuticals. In general, biopharmaceuticals are generally produced through a cultivation step and a subsequent separation-purification step. It is therefore coveted to establish an easy purification technology in a large scale in addition to a cultivation technology for improving an expression level of a target substance.

In order to purify a protein, a chromatographic isolation method is generally used, such as ion-exchange chromatography, hydrophobic interaction chromatography, reversed-phase chromatography, gel filtration chromatography and affinity chromatography. However, it is very difficult to obtain a pure target protein using only one purification technology, since there are many kinds of proteins in a culture medium after a cultivation step. Therefore, a purification process in which several methods are used in combination is generally employed (Patent Document 1).

Recently, an antibody drug has been actively developed as a medical protein. An antibody drug means a medicinal drug which utilizes a function of an antibody. An antibody drug reduces the side effects of a conventional medical drug and is expected to have a high therapeutic effect, since the antibody drug specifically acts on a target molecule.

An antibody drug actually contributes to an improvement of various disease conditions. However, with respect to an antibody drug, it is said that the purity thereof profoundly affects the quality in comparison with other medical proteins, since the antibody drug is administered to a living body in a large amount.

In order to produce a highly pure antibody, an affinity chromatography method, in which a molecule having a property to specifically bind to the target antibody is used as a ligand, is generally used. A monoclonal IgG antibody is mainly developed as an antibody drug, and Protein A which is produced by Staphylococcus is well-known as a ligand having an affinity for an IgG antibody.

For example, in an early stage of a purifying step, i.e. capturing step, of a process for producing an antibody drug, a column for affinity chromatography in which Protein A is immobilized as a ligand on a water-insoluble base material is generally used (Non-patent Document 1 and Non-patent Document 2). Hereinafter, such a column for affinity chromatography is referred to as "Protein A column".

However, Protein A needs a high producing cost; therefore, various technological developments are promoted to improve the properties of a column. For example, a ligand is modified in a protein engineered approach to increase an amount to be bound to a column (Patent Document 2 and Patent Document 3) and to improve an alkalinity-resistance for washing (Patent Document 4 and Patent Document 5).

On the other hand, a replacement for Protein A is developed. For example, a base material on which a synthesized low-molecular-weight compound having a property to bind to an antibody is marketed as MAbsorbent (trade mark) manufactured by ProMetic BioSciences Ltd.

As a low-molecular-weight compound which can bind to an antibody, a sulfone derivative (Patent Document 6), a triazine derivative (Patent Document 7), a mercapto heterocyclic ring compound (Patent Document 8), a 4-pyridylethylthioalkyl derivative (Non-patent Document 3) and a thiazole derivative (Patent Document 9) are well-known. The compounds are excellent in a chemical and physical stability.

However, there is fear that the above-described replacements for Protein A exhibit a non-specific adsorption depending on the basic structure thereof.

PRIOR ART

Patent Document

Patent Document 1: WO 2004/087761
Patent Document 2: U.S. Pat. No. 6,399,750 B
Patent Document 3: JP 2007-252368 A
Patent Document 4: EP 1123389 B
Patent Document 5: WO 03/080655
Patent Document 6: U.S. Pat. No. 4,696,980 B
Patent Document 7: JP 2009-531653 T
Patent Document 8: JP 3844496 B
Patent Document 9: JP 2009-244252 A

Non-Patent Document

Non-Patent Document 1: J. Chromatogr. B., 848, 48-63 (2007)
Non-Patent Document 2: J. Chromatogr. A., 1160, 44-55 (2007)
Non-Patent Document 3: Bioseparation, 9, 211-221 (2000)

DISCLOSURE OF THE INVENTION

Problems to be Solved by the Invention

Replacement ligands for protein A which have been developed so far are derivatives having a basic structure such as triazine and thiazole. Such replacements are still unsatisfactory as a ligand used for analyzing, purifying, characterizing, identifying or quantitating a protein. Accordingly, the objective of the present invention is to extensively develop various ligands which have a high chemical stability and which are versatile.

Means for Solving the Problems

The inventors of the present invention intensively studied for solving the above problem. As a result, the present inventors completed the present invention by finding that the low-molecular-weight compound having a general formula (1):

ArX-(Linker)-ArYHB  (1)

wherein ArX is a structure containing an optionally substituted aromatic six-membered ring, ArYHB is a structure containing an optionally substituted aromatic six-membered ring having a proton donor, the atom group "Linker" has not less than 4 and not more than 30 atoms and binds ArX with ArYHB,
specifically binds to an Fc region, i.e. IgG-Fc, of an IgG antibody. Accordingly, the present invention is as follows.
[1] Use of a low-molecular-weight compound represented by a general formula (1):

wherein ArX is a structure containing an optionally substituted aromatic six-membered ring, ArYHB is a structure containing an optionally substituted aromatic six-membered ring having a proton donor, the atom group "Linker" has not less than 4 and not more than 30 atoms and binds ArX with ArYHB,
for binding a proteinaceous substance.
[1] A method for binding a proteinaceous substance to a low-molecular-weight compound, comprising the step of contacting the low-molecular-weight compound represented by the above formula (1) with the proteinaceous substance.
[2] The use or the method described in the above [1], wherein the ArYHB in the low-molecular-weight compound has a structure formed by directly binding a hydroxy group or an amino group to the aromatic six-membered ring or a side chain thereof.
[3] The use or the method according to [1] or [2], wherein the ArX in the low-molecular-weight compound has any one of a halogen group, an amino group, a hydroxy group or a methyl group as a substituent, or the Arx has a structure containing any one of a benzene ring, a naphthalene ring or 1,2-methylenedioxybenzene, or the Arx has both of the substituent and the structure.
[4] The use or the method according to any one of [1] to [3], wherein the Linker is a structure containing optionally substituted tetrazole, optionally substituted hydantoin, optionally substituted pyrrol, optionally substituted pyridine, optionally substituted 1,3,4-thiadiazole, optionally substituted triazole, optionally substituted aminopyrazolo[3,4-d]pyrimidine, optionally substituted thiazole or optionally substituted pyrimidine, or is represented by —U—CZ—V—, wherein CZ is a structure containing an optionally substituted benzene ring or an optionally substituted naphthalene ring, and U and V are respectively composed of a non-hydrogen atom which does not contain a ring structure.
[5] The use or the method according to any one of [1] to [4], wherein the low-molecular-weight compound is any one of the compounds (2) to (17) represented by the following formulae:

(2)

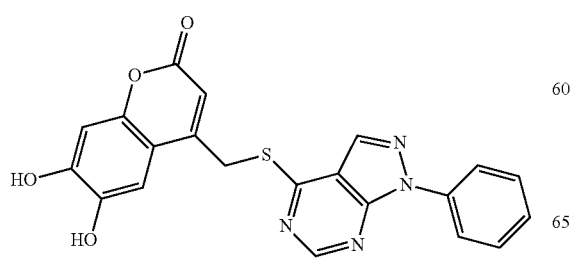

-continued (3)

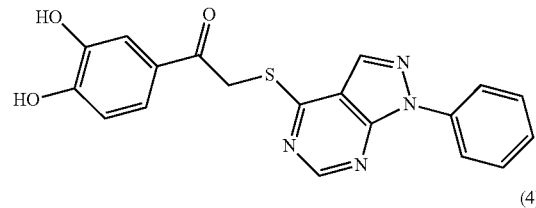

(4)

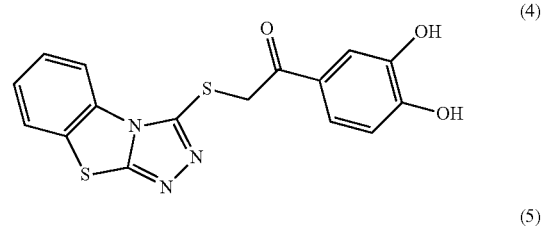

(5)

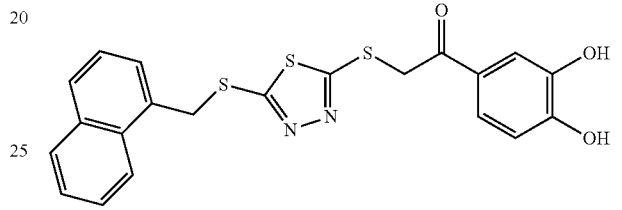

(6)

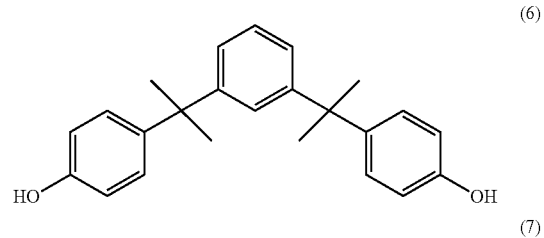

(7)

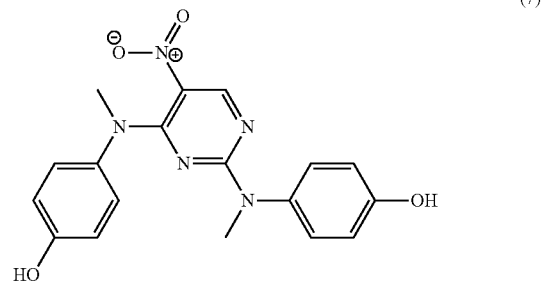

(8)

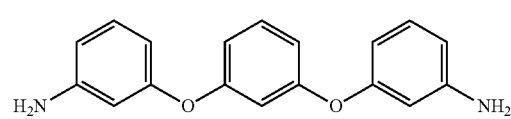

(9)

-continued

(10)
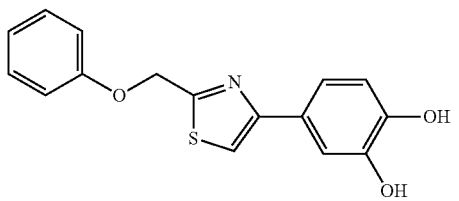

(11)
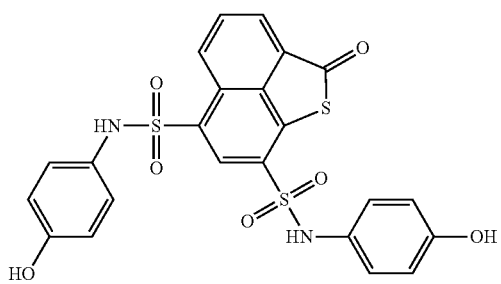

(12)
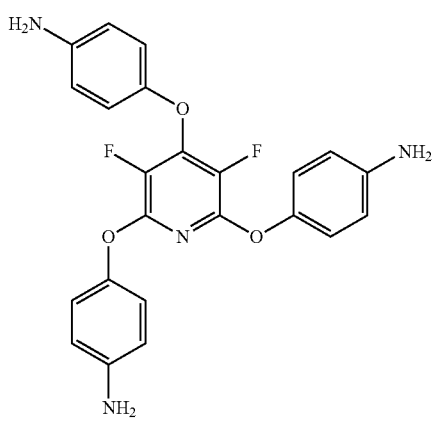

(13)
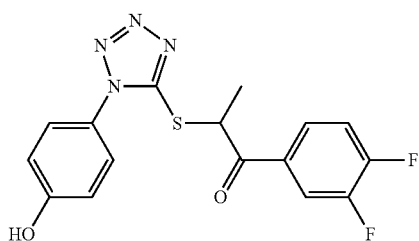

(14)
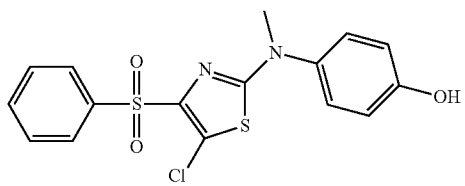

(15)
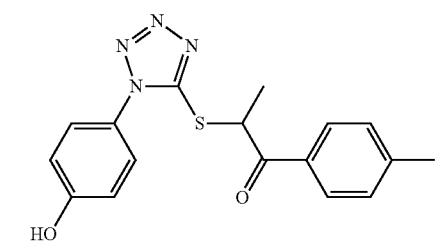

-continued

(16)
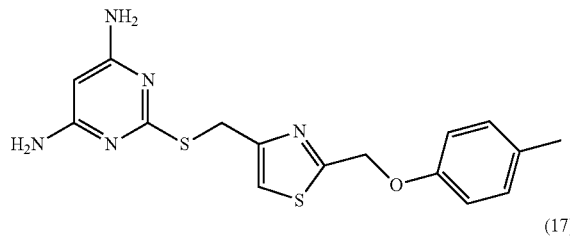

(17)
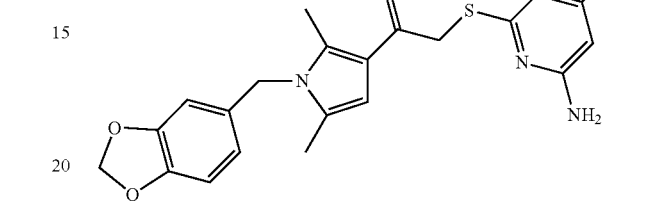

[6] The use or the method according to any one of [1] to [5], wherein the proteinaceous substance is an immunoglobulin or a fragment of an immunoglobulin.

[7] The use or the method according to any one of [1] to [6], wherein the proteinaceous substance is a monoclonal antibody.

[8] The use or the method according to any one of [1] to [7], wherein the proteinaceous substance is IgG-Fc or an Fc fusion protein.

[9] The use or the method according to any one of [1] to [8], wherein the proteinaceous substance is contained in a cell culture medium.

[10] An affinity separation matrix, wherein the low-molecular-weight compound according to any one of [1] to [9] is immobilized on a water-insoluble base material through a spacer binding to the "Linker" of the low-molecular-weight compound.

Effect of the Invention

The low-molecular-weight compound according to the present invention can be used as a useful and highly durable ligand for separating, recovering, isolating, purifying, characterizing, identifying or quantitating a proteinaceous substrate, particularly an immunoglobulin. In addition, by using the versatile low-molecular-weight compound with diversity, a selective adsorbent-desorbent for a proteinaceous substrate, particularly an immunoglobulin, can be produced with low cost and such a proteinaceous substrate can be industrially and effectively purified.

MODE FOR CARRYING OUT THE INVENTION

Figure 1:
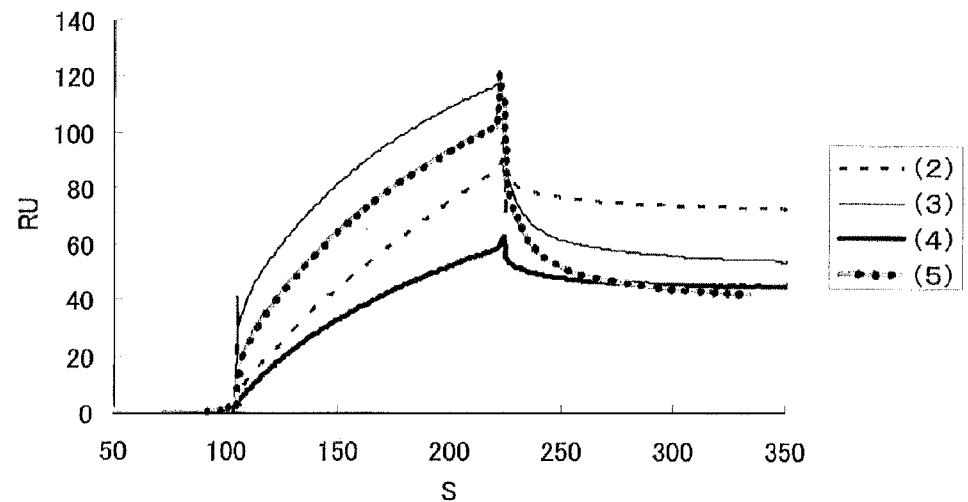
FIG. 1 demonstrates binding curves obtained by the Biacore measure experiment of Example 2 with respect to the low-molecular-weight compounds (2) to (5), which are IgG-Fc binding low-molecular-weight compounds.

Hereinafter, the definitions in the present invention are described.

The low-molecular-weight compound used in the present invention is the compound represented by the following formula (1):

ArX-(Linker)-ArYHB                                 (1).

In the above formula, ArX is a structure containing an optionally substituted aromatic six-membered ring, and ArYHB is a structure containing an optionally substituted aromatic six-membered ring having a proton donor.

The "Linker" is a structure which contains optionally substituted tetrazole, optionally substituted hydantoin, optionally substituted pyrrol, optionally substituted pyridine, optionally substituted 1,3,4-thiadiazole, optionally substituted pyrimidine such as 5-nitropyrimidine, optionally substituted triazole, optionally substituted aminopyrazolo[3,4-d]pyrimidine or optionally substituted thiazole, or is represented by "—U—CZ—V—", wherein CZ is a structure containing an optionally substituted benzene ring or an optionally substituted naphthalene ring, and U and V are respectively composed of a non-hydrogen atom which does not have a ring structure.

The compound represented by the above formula (1) can be used as a ligand which is useful and highly durable and which is used for separating, recovering, isolating, purifying, characterizing, identifying or quantitating a proteinaceous substrate, particularly an immunoglobulin. In addition, when the versatile low-molecular-weight compounds with diversity are used, a selective adsorbent-desorbent for a proteinaceous substrate, particularly an immunoglobulin, can be produced with low cost. Such an adsorbent-desorbent can be used for an industrial purification with advantage.

The binding property of the structure represented by the formula (1) to a proteinaceous substrate is not clearly elucidated. It is however thought that the structure of formula (1) containing two aromatic six-membered rings of ArX and ArYHB may effectively act, since Protein A, which interacts with IgG-Fc, partially has a continuous structure of phenylalanine-tyrosine.

Hereinafter, the ArX, ArYHB and Linker in the formula (1) are described.

The "ArX" is a structure containing an optionally substituted aromatic six-membered ring. The position, kind and number of the substituent is not particularly limited. In addition, the ArX may be a condensed aromatic structure or any one of a hydrocarbon ring or a heterocyclic ring as long as the ArX partly has an aromatic six-membered ring. The aromatic six-membered ring may have various substituents, for example, a halogen group such as a fluorine group, a chlorine group, a bromine group and an iodine group; a non-proton polar group such as a nitro group, a nitrile group, a carboxylate ester group, a sulfonate ester group and an alkoxy group; a proton donor such as an amino group, a hydroxy group, a thiol group, a carboxylate group and a sulfonate group; and a hydrocarbon group such as a methyl group and an ethyl group.

In particular, it is preferred for an excellent binding property to an immunoglobulin that the ArX has (i) any one substituent selected from a halogen group (preferably a fluorine group, a chlorine group or a bromine group, particularly a fluorine group or a chlorine group), a proton donor (preferably an amino group or a hydroxy group) and a $C_{1-4}$ hydrocarbon group (preferably a methyl group), or (ii) a structure containing a benzene ring unit, for example, a structure containing any one selected from a benzene ring, a naphthalene ring and 1,2-methylenedioxybenzene represented by the following formula (18):

or both of the substituent (i) and the structure (ii). It is particularly preferred that the Arx is a hydrocarbon ring such as a benzene ring and a naphthalene ring, and a proton donor such as an amino group and a hydroxy group does not bind to the hydrocarbon ring.

The "ArYHB" is an optionally substituted aromatic six-membered ring having a proton donor. The proton donor is exemplified by the proton donor exemplified in the above description about ArX, and is preferably an amino group or a hydroxy group. The proton donor group may directly bind to the aromatic six-membered ring or a side chain of the six-membered ring, and it is preferred that the proton donor group directly binds to the six-membered ring. The kind of a substituent of the ArYHB is not particularly limited. The substituent is exemplified by the substituent of the ArX other than a proton donor. The position and number of the substituent are also particularly not limited. The preferred substituent is a halogen group, more preferably a fluorine group, a chlorine group or a bromine group, and particularly a bromine group.

The aromatic six-membered ring of the ArYHB may be, for example, a condensed aromatic structure, a cyclic hydrocarbon ring such as a benzene ring, or a heteroaromatic six-membered ring. The aromatic six-membered ring is preferably a non-condensed hydrocarbon ring or a non-condensed heterocyclic ring.

In particular, as a structure which has excellent binding property to an immunoglobulin, a non-condensed aromatic six-membered ring in which a hydroxy group or an amino group as a proton donor directly binds to the ring structure is preferred, since there is partly tyrosine having a proton donor in a structure of Protein A which interacts with IgG-Fc.

The atom group "Linker" has not less than 4 and not more than 30 atoms and binds the ArX with the ArYHB, and may be linear, branched or cyclic. The kind of binding in the "Linker" and between the "Linker" and the ArX or the ArYHB is not limited. The "Linker" and the ArX or the ArYHB may be bound at one position or two positions. In particular, as a structure which has an excellent binding property to an immunoglobulin in the present invention, a ring structure containing optionally substituted tetrazole, optionally substituted hydantoin, optionally substituted pyrrol, optionally substituted pyridine, optionally substituted 1,3,4-thiadiazole, optionally substituted pyrimidine such as 5-nitropyrimidine, optionally substituted triazole, optionally substituted aminopyrazolo[3,4-d]pyrimidine, optionally substituted thiazole, or a structure represented by "—U—CZ—V—" is preferred, since the structures have a planarity and is difficult to be flexible. The "CZ" is a structure containing an optionally substituted benzene ring or an optionally substituted naphthalene ring, and both of the "U" and "V" are respectively composed of a non-hydrogen atom which does not have a ring structure. Such a non-hydrogen atom is exemplified by —O—, —S—, —SO—, —SO$_2$—, —NH—, —NR—, —CH$_2$—, —CHR— and —CR$_2$—, and preferably a group in which a hydrogen atom is not bound on a binding chain, such as —O—, —S—, —SO—, SO$_2$—, —NR— and —CR$_2$—, wherein R is an organic group having an alkyl group such as a methyl group. The "U" and "V" may be composed of one non-hydrogen atom or continuous not less than two, particularly two, non-hydrogen atoms.

It is possible by chemical modification to further improve the binding property of the low-molecular-weight compound represented by the formula (1) to an immunoglobulin.

It is reported that a low-molecular-weight ligand described in a prior art non-specifically adsorbs a component except for an antibody (J. Chromatogr. A 2007, 1162, 24-33). On the other hand, when the compound represented by the formula (1), particularly the structures represented by the formulae (6), (7), (9), (11), (12), (13), (14) and (15), is used, a non-specific adsorption, for example, a non-specific adsorption with substance except for an immunoglobulin in a culture supernatant, is suppressed. It is thought as the reason for such a suppression that both of a binding property and a selectivity to IgG-Fc are improved, since the "Linker" in addition to the Arx and ArYHB also interacts with IgG-Fc.

The preferred low-molecular-weight compound (1) is exemplified by the following compounds (101), (201), (301) and (401).

The compound (101) is represented by the following formula.

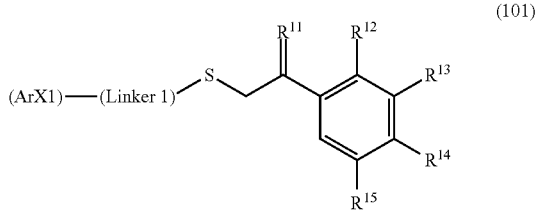

(101)

In the above formula, the ArX1 is the same as the above ArX. The "Linker 1" is a divalent group of the ring structure which is exemplified as the above "Linker" and which is bound by "—S—". $R^{11}$ is a carbon atom or an oxygen atom; and when $R^{11}$ is a carbon atom, $R^{12}$ binds to the carbon atom. $R^{12}$ is a hydrogen atom or an organic group which forms a ring with $R^{11}$. $R^{13}$ to $R^{15}$ may be the same or different each other, and are a hydrogen atom or a proton donor, particularly an amino group or a hydroxy group; and at least one of $R^{13}$ to $R^{15}$ is a proton donor.

The ArX1 is preferably an aromatic hydrocarbon ring such as a benzene ring and a naphthalene ring.

The "Linker 1" is preferably optionally substituted 1,3,4-thiadiazole, optionally substituted triazole, or optionally substituted aminopyrazolo[3,4-d]pyrimidine. The "Linker 1" and ArX1 may be bound directly or through other bond such as an ether bond, a thioether bond, a methylene chain and a combination thereof. The other bond is preferably a thioether bond or a bond consisting of a thioether bond and a methylene chain. In addition, when the ArX1 and the "Linker" are bound at two positions, the groups may be directly bound at one position and through other bond at the other position.

When $R^{11}$ and $R^{12}$ form a ring, the formed ring is preferably a five- or six-membered ring, and more preferably a tetrahydro-δ-valerolactone ring.

It is preferred that at least two of $R^{13}$ to $R^{15}$ are proton donors, and it is more preferred that adjacent two are proton donors.

The compound (101) is specifically exemplified by the compounds (2), (3), (4) and (5) described later.

The compound (201) is represented by the following formula.

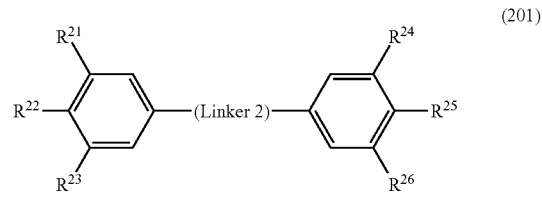

(201)

The "Linker 2" is the ring structure exemplified as the above "Linker" or a divalent group which is formed by binding the above "U" group and the "V" group to the ring structure. $R^{21}$ to $R^{26}$ may be the same or different each other, and is a hydrogen atom or a proton donor, particularly an amino group or a hydroxy group, and at least one of $R^{24}$ to $R^{26}$ is a proton donor.

The "Linker 2" is preferably "—U—CZ—V—", optionally substituted pyrimidine (particularly 5-nitropyrimidine) optionally substituted pyridine (for example, pyridine which may be optionally substituted by a halogen atom such as a fluorine atom or an alkoxy group such as p-aminophenyleneoxide. In the compound (201), the above-described pyrimidine or pyridine is respectively bound by the "U" group and "V" group. The "U" and "V" are preferably one or two selected from —O—, SO$_2$—, —NH—, —NR— and —CR$_2$—, and more preferably one or two selected from —O—, SO$_2$—, —NR— and —CR$_2$—. The "CZ" in "—U—CZ—V—" is preferably a benzene ring, a naphthalene ring or a substituted naphthalene ring. The substituted naphthalene ring is particularly a naphthalene ring which is crosslinked at 1 position and 8 position to form a five- or six-membered ring, for example, a naphthalene ring which is crosslinked by —S—C(=O)— at 1 position and 8 position.

It is preferred that at least one of $R^{21}$ to $R^{23}$ is a proton donor. When any one of $R^{21}$ to $R^{23}$ is a proton donor, it is preferred that the proton donors of $R^{21}$ to $R^{23}$ and $R^{24}$ to $R^{26}$ are the same each other.

The compound (201) is specifically exemplified by the compounds (6), (7), (8), (11) and (12) described later.

The compound (301) is represented by the following formula.

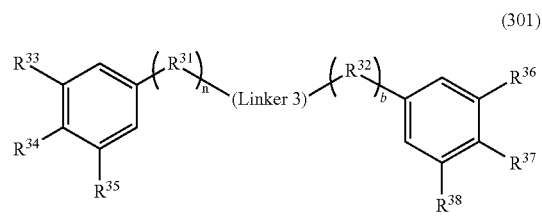

(301)

In the formula, the "Linker 3" is the ring structure exemplified as the above "Linker". $R^{31}$ and $R^{32}$ may be the same or different each other, and is one of the above-described non-hydrogen atom or =CH— group. When there are two or more $R^{31}$, the groups may be the same or different each other. The same definition is applicable to the case where there are two or more $R^{32}$. The "a" and "b" are 0 or an integer of not less than 1. $R^{33}$ to $R^{38}$ may be the same or different each other, and is a hydrogen atom, a proton donor (particularly an amino group or a hydroxy group), a halogen atom such as a chlorine group and a bromine group, or a hydrocarbon group (particularly a methyl group), and at least one of $R^{36}$ to $R^{38}$ is a proton donor.

The "Linker 3" is preferably optionally substituted hydantoin or optionally substituted thiazole. The $(R^{31})_a$ and $(R^{32})_b$ are preferably —$CH_2$—, =CH—, —$SO_2$—, —$N(CH_3)$—, —$CH_2$—O—, —$CH_2$—S—.

The compound (301) is specifically exemplified by the compounds (9), (10), (14) and (16) described later.

The compound (401) is represented by the following formula.

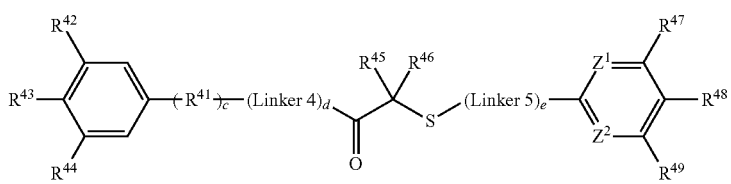

(401)

In the formula, the "Linker 4" and "Linker 5" are the ring structures exemplified as the above "Linker". $R^{41}$ is one of the above-described non-hydrogen atoms. The "c" is 0 or 1, and each of "d" or "e" is 1 and the other is 0. $R^{42}$ to $R^{49}$ may be the same or different each other, and is a hydrogen atom, a proton donor (particularly an amino group or a hydroxy group), a halogen atom (particularly a fluorine group), a hydrocarbon group (particularly a methyl group) or an alkoxy group. Two selected from $R^{42}$ to $R^{44}$ may be bound to form a ring, and two selected from $R^{47}$ to $R^{48}$ may be bound to form a ring. In addition, at least one of $R^{47}$ to $R^{49}$ is a proton donor.

The "Linker 4" and "Linker 5" are preferably optionally substituted tetrazole, optionally substituted pyrrol (particularly dimethylpyrrol). $R^{41}$ is preferably —$CH_2$—.

The compound (401) is specifically exemplified by the compounds (13), (15) and (17) described later.

The low-molecular-weight compound according to the present invention is typically exemplified by the structures of the following formula (2) to (17):

(2)

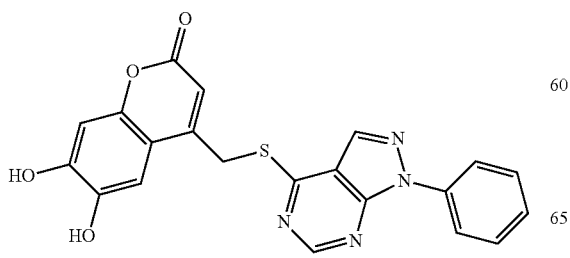

(3)

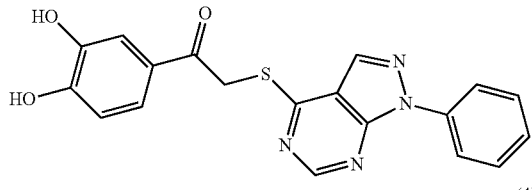

(4)

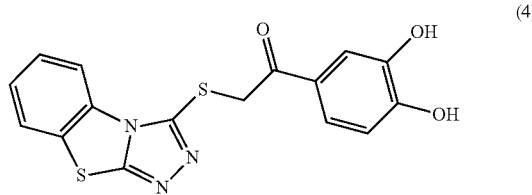

-continued (5)

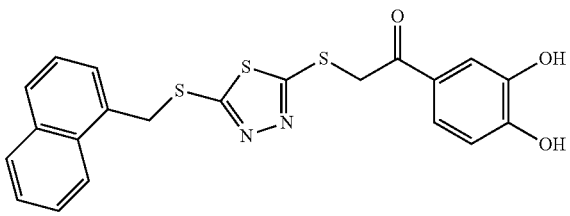

(6)

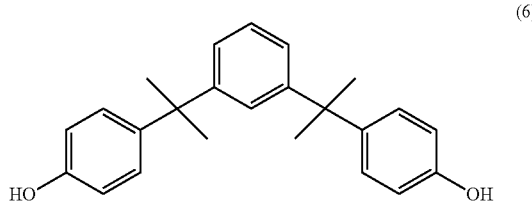

(7)

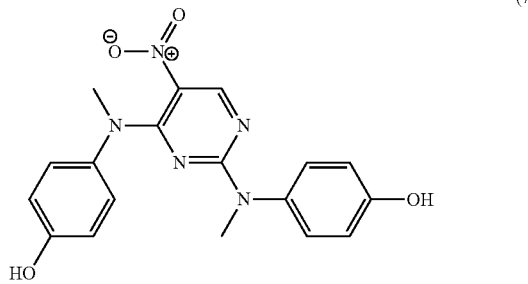

(8)

-continued

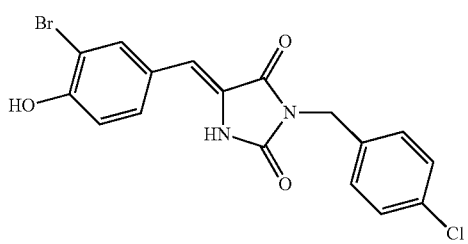
(9)

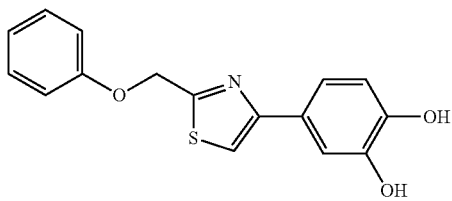
(10)

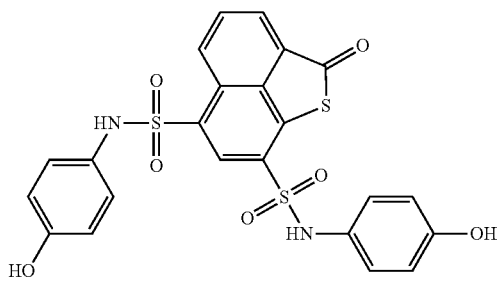
(11)

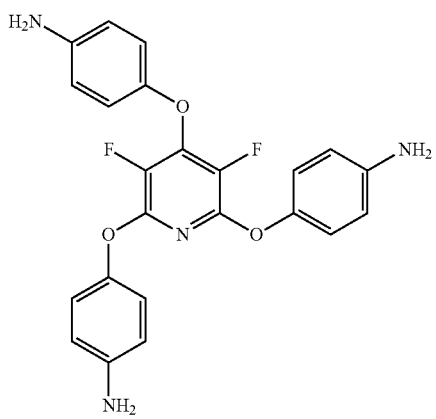
(12)

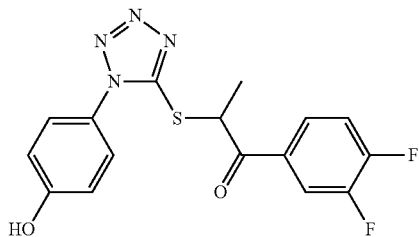
(13)

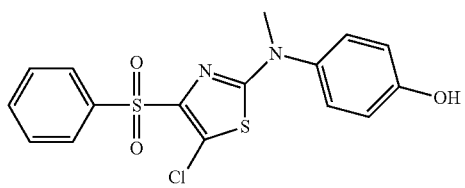
(14)

-continued

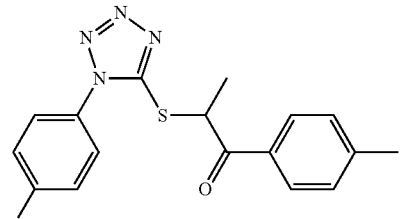
(15)

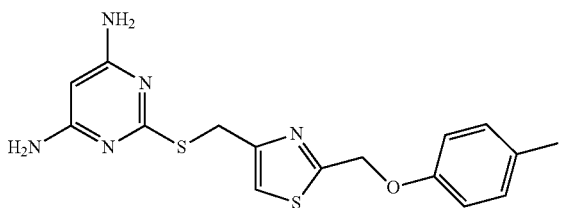
(16)

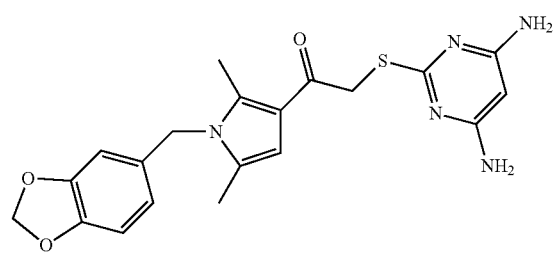
(17)

In the above formulae, the ArX, ArYHB and "Linker" are as follows.

(2) ArX=a benzene ring, ArYHB=a substituted six-membered aromatic ring to which hydroxy groups are bound, "Linker"=aminopyrazolo[3,4-d]pyrimidine;

(3) ArX=a benzene ring, ArYHB=a substituted six-membered aromatic ring to which hydroxy groups are bound, "Linker"=aminopyrazolo[3,4-d]pyrimidine;

(4) ArX=a benzene ring, ArYHB=a substituted six-membered aromatic ring to which hydroxy groups are bound, "Linker"=triazole;

(5) ArX=a naphthalene ring, ArYHB=a substituted six-membered aromatic ring to which hydroxy groups are bound, "Linker"=1,3,4-thiadiazole;

(6) ArX=a six-membered aromatic ring having a hydroxy group as a substituent, ArYHB=a six-membered aromatic ring to which a hydroxy group is bound, "Linker"=a benzene ring;

(7) ArX=a six-membered aromatic ring having a hydroxy group as a substituent, ArYHB=a six-membered aromatic ring to which a hydroxy group is bound, "Linker"=nitropyrimidine;

(8) ArX=a six-membered aromatic ring having an amino group as a substituent, ArYHB=a six-membered aromatic ring to which an amino group is bound, "Linker"=a benzene ring;

(9) ArX=a six-membered aromatic ring having a halogen group as a substituent, ArYHB=a substituted six-membered aromatic ring to which a hydroxy group is bound, "Linker"=hydantoin;

(10) ArX=a benzene ring, ArYHB=a substituted six-membered aromatic ring to which hydroxy groups are bound, "Linker"=triazole;

(11) ArX=a six-membered aromatic ring having a hydroxy group as a substituent, ArYHB=a six-membered aromatic ring to which a hydroxy group is bound, "Linker"=a substituted naphthalene ring;
(12) ArX=a six-membered aromatic ring having an amino group as a substituent, ArYHB=a six-membered aromatic ring to which an amino group is bound, "Linker"=pyridine;
(13) ArX=a six-membered aromatic ring having halogen groups as substituents, ArYHB=a six-membered aromatic ring to which a hydroxy group is bound, "Linker"=tetrazole;
(14) ArX=a benzene ring, ArYHB=a six-membered aromatic ring to which a hydroxy group is bound, "Linker"=thiazole;
(15) ArX=a six-membered aromatic ring having a methyl group as a substituent, ArYHB=a six-membered aromatic ring to which a hydroxy group is bound, "Linker"=tetrazole;
(16) ArX=a six-membered aromatic ring having a methyl group as a substituent, ArYHB=a six-membered aromatic ring to which amino groups are bound, "Linker"=thiazole;
(17) ArX=a structure represented by the formula (18), ArYHB=pyrimidine, which is a six-membered heteroaromatic ring, to which amino groups are bound, "Linker"=pyrrol.

As the low-molecular-weight compound according to the present invention, the compound (101) and the compound (201) are particularly preferred. It is preferred that the "Linker 2" of the compound (201) is formed by binding the U group and the V group to an optionally substituted benzene ring or an optionally substituted pyrimidine ring. The most preferred low-molecular-weight compound is anyone of the compounds (2), (3), (4), (5), (6), (7) and (8). The preferred low-molecular-weight compounds have a particularly high binding property to IgG-Fc.

The present invention also relates to various methods for using the low-molecular-weight compound which is represented by the formula (1) and which has a high affinity for an Fc region of an immunoglobulin for binding a proteinaceous substance.

In the present invention, the term "a proteinaceous substrate" means any molecule which has a polypeptide structure, and a fragmented peptide and a polypeptide chain which is bound by a peptide bond are included in the proteinaceous substrate. The proteinaceous substrate is exemplified by an immunoglobulin, an immunoglobulin fragment, a monoclonal antibody, a protein which has an Fc region (IgG-Fc) of an immunoglobulin, and an Fc-fused protein. The proteinaceous substrate may be contained in a cell incubation medium.

A three-dimensional protein structure of an antibody is well-known; therefore, a Fab region or an Fc region may be further modified, for example, fragmented, while the three-dimensional protein structure thereof is maintained. In other words, the proteinaceous substrate of the present invention is not limited to an immunoglobulin molecule which has a complete Fab region and Fc region or a derivative thereof.

Therefore, the term "a protein which has an Fc region (IgG-Fc) of an immunoglobulin" means a protein which has an Fc region side, and it is not necessary that the protein has a complete Fc region as long as the low-molecular-weight compound can bind to the protein. In addition, as long as the protein has an Fc region, the protein may be an Fc region-fused compound or an Fc region-fused inorganic compound which is obtained by a synthesis or the like.

An affinity for an immunoglobulin can be evaluated using a device for detecting or analyzing an interaction between biomolecules. For example, such a device is exemplified by a biosensor which utilizes a surface plasmon resonance principle, such as Biacore system manufactured GE Healthcare Company, and an isothermal titration calorimeter, i.e. ITC, which detects a change of exotherm and endotherm generated by a binding.

The present invention also related to an affinity ligand which utilizes properties of the above-described low-molecular-weight compound. In other words, the present invention relates to an affinity separation matrix characterized in being formed by immobilizing the "Linker" part of the ligand (low-molecular-weight compound) on a water-insoluble base material through a spacer.

The term "affinity ligand" means a substance or a functional group which can selectively capture or bind to a target molecule from a mixture of molecules due to a specific affinity between molecules, such as a binding between an antigen and an antibody. In the present invention, the affinity ligand particularly means the low-molecular-weight compound represented by the formula (1), which can specifically bind to an immunoglobulin.

In the present invention, the description of a mere "ligand" means an "affinity ligand".

A water-insoluble material used in the present invention is exemplified by an inorganic base material such as glass beads and a silica gel; a synthetic polymer such as a cross-linked polyvinyl alcohol, a crosslinked polyacrylate, a crosslinked polyacrylamide, a crosslinked polystyrene, a polymethacrylate and a polyurethane; an organic base material consisting of a polysaccharide, such as crystalline cellulose, crosslinked cellulose, crosslinked agarose and crosslinked dextran; and a complex base material such as an organic-organic base material and an organic-inorganic base material, which can be obtained from a combination of the above-described base materials.

As the water-insoluble base material, a commercially available product may be used. Such a commercially available product is exemplified by GCL2000, which is composed of a porous cellulose gel; Sephacryl S-1000, which is obtained by covalently crosslinking allyl dextran and methylene bis-acrylamide; Toyopearl, which is an acrylate base material; Sepharose CL4B, which is a crosslinked agarose base material; and Cellufine, which is a crosslinked cellulose base material.

It is preferred that the water-insoluble base material used in the present invention has a large surface area and a large number of fine pores having an appropriate size to be porous from the view point of the intended use and method of the affinity separation matrix. A form of the base material is not limited and may be any one of beads, a monolith, a fiber and a film such as a hollow fiber.

For example, the ligand is immobilized on a base material by introducing a spacer molecule having an amino group, a carboxy group or a thiol group into the "Linker" of the low-molecular-weight compound and then carrying out a conventional coupling method.

The term "spacer" specifically means a molecule for binding the low-molecular-weight compound to a matrix and is exemplified by a compound having a reactive functional group such as an amino group, a carboxy group, an ether group and a thioether group.

The spacer molecule may be composed of two or more atoms.

For example, the coupling method may be carried out by reacting a base material with cyanogen bromide, epichlorohydrin, diglycidyl ether, tosyl chloride, tresyl chloride, hydrazine, sodium periodate or the like to activate the base material or to introduce a reactive functional group on a surface of the base material, and then carrying out a coupling reaction with the low-molecular-weight compound to be immobilized as a ligand; or adding a condensing reagent such as a carbodiimide or a reagent having plurality of functional groups in the molecule, such as glutaraldehyde, to a mixture of the base material and the low-molecular-weight compound to be immobilized as a ligand for condensation or crosslinking.

As the above description, the low-molecular-weight compound used as a ligand in the present invention may be immobilized by chemically modifying a base material or introducing a spacer molecule which is useful for the immobilization. In the present invention, the function of the low-molecular-weight compound is given to the matrix on which the low-molecular-weight compound is immobilized as a ligand. Any cases of the low-molecular-weight compound which is modified or changed for the immobilization are included in the range of the present invention.

An antibody, an antibody derivative, a fragmented antibody and a fragmented antibody derivative which have an Fc region (IgG-Fc) of an immunoglobulin can be separated, purified and characterized by an affinity column chromatography purification method using the affinity separation matrix, which is produced by immobilizing the low-molecular-weight compound according to the present invention on a water-insoluble base material.

In the present invention, the term "antibody derivative" is exemplified by a chimeric antibody obtained by partly displacing a domain of a human IgG by a domain of an IgG antibody derived from other organism to be fused, and a humanized antibody obtained by displacing a CDR part of a human IgG by a CDR part of an antibody derived from other organism to be fused. The "fragmented antibody" is exemplified by a protein consisting of only an Fc region (IgG-Fc) of a human IgG. The "fragmented antibody derivative" is exemplified by an artificial antibody obtained by fusing an Fv region and an Fc region of a human IgG.

The above antibody, antibody derivative, fragmented antibody and fragmented antibody derivative can be purified in accordance with a protocol which is equivalent to an affinity column chromatography purification method using a commercially available Protein A column (Roque A. C. A. et. al., Journal of Chromatography A, 2007, vol. 1160, pp. 44-55).

Specifically, a buffer solution containing the above antibody, antibody derivative, fragmented antibody and fragmented antibody derivative is adjusted to be neutral, and then the solution is passed through an affinity column which is filled with the affinity separation matrix according to the present invention in order to adsorb the antibody, antibody derivative, fragmented antibody and fragmented antibody derivative.

Subsequently, an appropriate amount of a pure buffer solution is passed through the affinity column in order to wash out the inside of the column. At the time, the target antibody, antibody derivative, fragmented antibody and fragmented antibody derivative is adsorbed on the affinity separation matrix according to the present invention in the column.

Then, an acidic buffer solution of which pH is appropriately adjusted is passed through the column in order to elute the target antibody, antibody derivative, fragmented antibody and fragmented antibody derivative. As a result, the target compound can be highly purified. The above acidic buffer solution may contain a substance to accelerate the elution from the matrix if necessary.

By a similar method to the above, an antibody, antibody derivative, fragmented antibody and fragmented antibody derivative which are adsorbed on the affinity separation matrix according to the present invention can be characterized in having IgG-Fc.

The affinity separation matrix according to the present invention is reusable by passing a pure buffer solution which has appropriate strong acidity or strong alkalinity and which does not completely impair the function of the ligand (low-molecular-weight compound) and the base material, in order to wash the column. The buffer may possibly contain an appropriate denaturating agent or an organic solvent.

It is predictable that when the low-molecular-weight compound according to the present invention is used as a ligand, the ligand exhibits a chemical stability higher than a ligand of a protein such as Protein A. The term "chemical stability" means a property for maintaining the function of the low-molecular-weight compound.

In the present invention, the term "maintaining the function of the low-molecular-weight compound" means to maintain an affinity for an Fc region (IgG-Fc) of an immunoglobulin. In addition, if the ligand has high "chemical stability", the affinity of the ligand for an Fc region (IgG-Fc) of an immunoglobulin is hardly decreased even when the ligand is subjected to various chemical treatments.

The present application claims the benefit of the priority date of Japanese patent application No. 2011-066589 filed on Mar. 24, 2011, and all of the contents of the Japanese patent application No. 2011-066589 filed on Mar. 24, 2011, are incorporated by reference.

EXAMPLES

Example 1

Production of an Fc Fragment Derived from Human Plasma

The "affinity for an Fc region" in the present invention was evaluated using an Fc fragment which did not have a Fab region of an immunoglobulin. An Fc fragment was prepared by fragmenting an IgG preparation derived from human plasma as a raw material into a Fab fragment and an Fc fragment using papain and separating the Fc fragment only to be purified. Gammagard, which is an IgG preparation derived from human plasma and which was manufactured by Baxter, was dissolved into a buffer solution for papain digestion which contained 0.1 M AcOH—AcONa, 2 mM EDTA and 1 mM cysteine and of which pH was 5.5, and Papain Agarose from papaya latex (papain-immobilized agarose, manufactured by SIGMA) was added to the solution. The mixture was mixed using a rotator and incubated at 37° C. for about 8 hours. The reaction mixture, which contained both of a Fab fragment and an Fc fragment, was separated from the papain-immobilized agarose. The Fc fragment was separated to be purified from the reaction mixture by affinity chromatography using Protein A column (MabSelect, manufactured by GE Healthcare Company). Hereinafter, the Fc fragment is referred to as "IgG-Fc". Specifically, the reaction mixture, which contained both of a Fab fragment and an Fc fragment, was diluted with a phosphate buffer (20 mM $NaH_2PO_4$—$Na_2HPO_4$, 150 mM NaCl, pH 7.4) so that the pH became about 7.4. The diluted mixture was added to a Protein A column which was equilibrated using a phosphate buffer, and the column was washed with a phosphate buffer. Then, an IgG-Fc solution was obtained by using an eluent buffer B (100 mM citric acid, pH 3.0) to elute the IgG-Fc. The above-described protein purification by chromatography was carried out using AKTAprime plus system manufactured by GE Healthcare Company.

Example 2

Analysis of the Affinity of the Low-Molecular-Weight Compound for IgG-Fc

The analysis of the affinity between the low-molecular-weight compound and IgG-Fc was carried out using Biacore 3000, which was manufactured by GE Healthcare Company and in which surface plasmon resonance was utilized, under the following protocol. All of the sensor chip and reagents used in the following protocol were manufactured by GE Healthcare Company. The low-molecular-weight compounds (2) to (17) of which binding properties were evaluated were obtained from Namiki Shoji Co., Ltd.

The IgG-Fc obtained in the Example 1 was diluted 50-fold with a buffer for immobilization (10 mM $CH_3COOH$—$CH_3COONa$, pH 4.5), and the IgG-Fc was immobilized on a sensor chip CM5 in accordance with the protocol provided with Biacore 3000. The immobilization of the IgG-Fc on the sensor chip CM5 was carried out by amine coupling method using N-hydroxysuccinimide (NHS) and N-ethyl-N'-(3-dimethylaminopropyl)carbodiimide hydrochroride (EDC), and ethanolamine was used for blocking. In addition, a reference cell was prepared as a negative control by activating other flow cell on a chip by EDC/NHS and then immobilizing ethanolamine.

Figure 2:
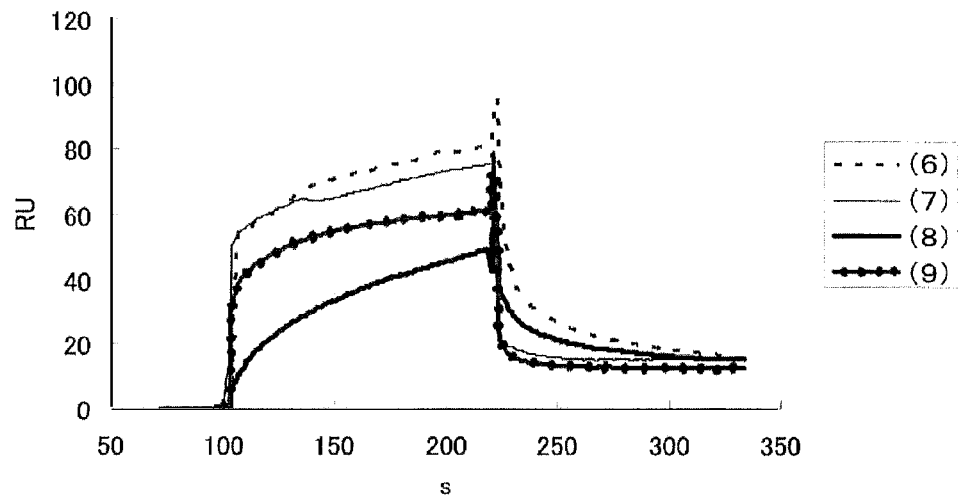
FIG. 2 demonstrates binding curves obtained by the Biacore measure experiment of Example 2 with respect to the low-molecular-weight compounds (6) to (9), which are IgG-Fc binding low-molecular-weight compounds.
Figure 3:
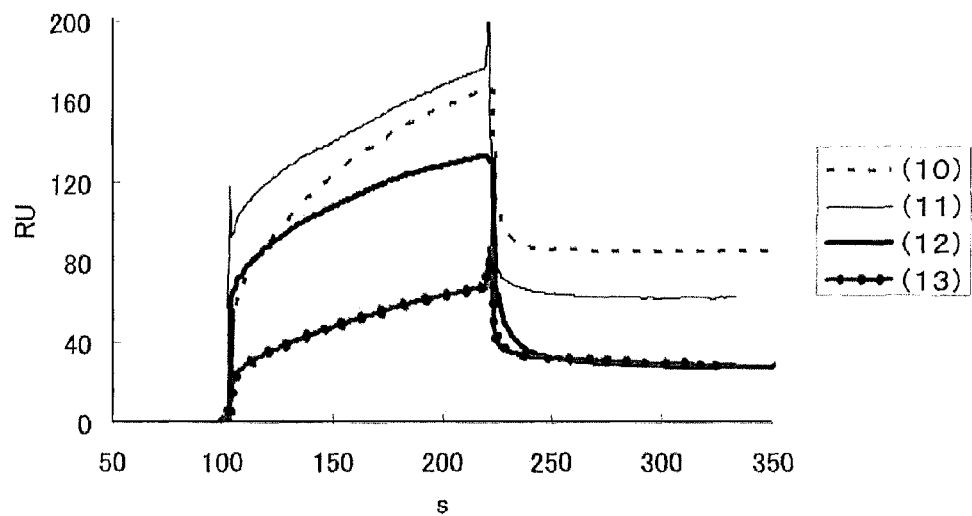
FIG. 3 demonstrates binding curves obtained by the Biacore measure experiment of Example 2 with respect to the low-molecular-weight compounds (10) to (13), which are IgG-Fc binding low-molecular-weight compounds.
Figure 4:
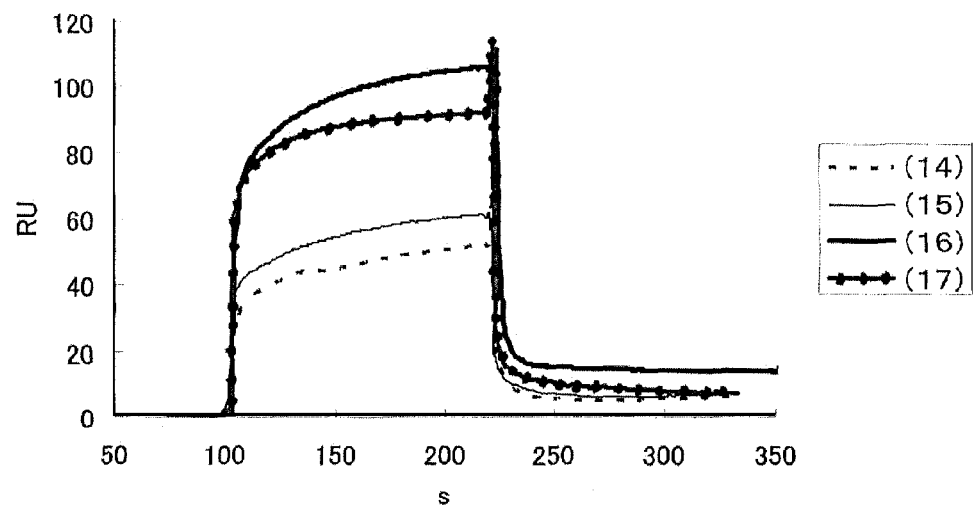
FIG. 4 demonstrates binding curves obtained by the Biacore measure experiment of Example 2 with respect to the low-molecular-weight compounds (14) to (17), which are IgG-Fc binding low-molecular-weight compounds.

A ligand of any one of the low-molecular-weight compounds (2) to (17) was flowed on the above sensor chip to detect an interaction. Specifically, each of the low-molecular-weight compound (2) to (17) to be measured was diluted with a running buffer (20 mM $NaH_2PO_4$—$Na_2HPO_4$, 150 mM NaCl, 0.005% P-20, 5% DMSO, pH 7.4) to prepared three or four kinds of diluted solutions of which concentrations were different each other within the range of 25 μM to 100 μM with respect to each compound. The prepared solutions of the each low-molecular-weight compound were added to the sensor chip at a flow rate of 30 μL/min for 120 seconds. Binding reaction curves were orderly observed at the time of addition (binding phase, for 120 seconds) and after the addition (dissociation phase, for 120 second) at the measurement temperature of 25° C. After the each observation, 40 mM NaOH was added for 15 seconds to regenerate the sensor chip. A binding reaction curve of a sample containing DMSO was corrected using a Biacore correction tool manufactured by GE Healthcare Company with respect to the obtained binding curves (see FIGS. 1 to 4). In the Figures, "S" of the horizontal axis represents an elapsed time (sec) for the detection (measurement), and "RU" of the vertical axis represents a detected intensity. A coupling constant: $K_A = K_{on}/K_{off}$ was calculated by carrying out a fitting analysis of the corrected binding reaction curve with a binding model of 1:1 using BIA evaluation, which was a software provided with the system. The result is shown in Table 1.

TABLE 1

| Result of Biacore mearuerment experiment | |
|---|---|
| IgG-Fc binding low-molecular-weight compound | $K_A \times 10^4$ (M$^{-1}$) |
| (2) | 13 |
| (3) | 5.1 |
| (4) | 5.1 |
| (5) | 4.6 |
| (6) | 2.9 |
| (7) | 0.96 |
| (8) | 0.95 |
| (9) | 0.48 |
| (10) | 0.4 |
| (11) | 0.37 |
| (12) | 0.2 |
| (13) | 0.17 |
| (14) | 0.16 |
| (15) | 0.12 |
| (16) | 0.06 |
| (17) | 0.05 |

As the result shown in Table 1, the values of the binding constant: $K_A$ of the each low-molecular-weight compounds (2) to (17) were about $10^3$ to $10^4$ M$^{-1}$. The result demonstrates that the low-molecular-weight compounds have a strong binding property to IgG-Fc.

What is claimed is:

1. A method for binding an IgG-Fc or an Fc fusion protein to a low-molecular-weight compound, comprising contacting a low-molecular-weight compound represented by the general formula (I):

ArX-(Linker)-ArYHB (1)

wherein

ArX is a structure containing an optionally substituted aromatic six-membered ring, ArYHB is a structure containing an optionally substituted aromatic six-membered ring having a proton donor, the atom group "Linker" is a structure containing optionally substituted tetrazole, optionally substituted hydantoin, optionally substituted pyrrol, optionally substituted pyridine, optionally substituted 1,3,4-thiadiazole, optionally substituted triazole, optionally substituted aminopyrazolo[3,4-d]pyrimidine, optionally substituted thiazole or nitropyrimidine, or is represented by —U—CZ—V—, wherein CZ is a structure containing an optionally substituted benzene ring or an optionally substituted naphthalene ring, and U and V are respectively composed of a non-hydrogen atom not containing a ring structure and binds ArX with ArYHB, with the IgG-Fc or Fc fusion protein.

2. The method according to claim 1, wherein the ArYHB in the low-molecular-weight compound has a structure formed by directly binding a hydroxy group or an amino group to the aromatic six-membered ring or a side chain thereof.

3. The method according to claim 1, wherein the ArX in the low-molecular-weight compound has any one of a halogen group, an amino group, a hydroxy group or a methyl group as a substituent, or the Arx has a structure containing any one of a benzene ring, a naphthalene ring or 1,2-methylenedioxybenzene, or the Arx has both of the substituent and the structure.

4. The method according to claim 1, wherein the low-molecular-weight compound is any one of the compounds (2) to (17) represented by the following formulae:

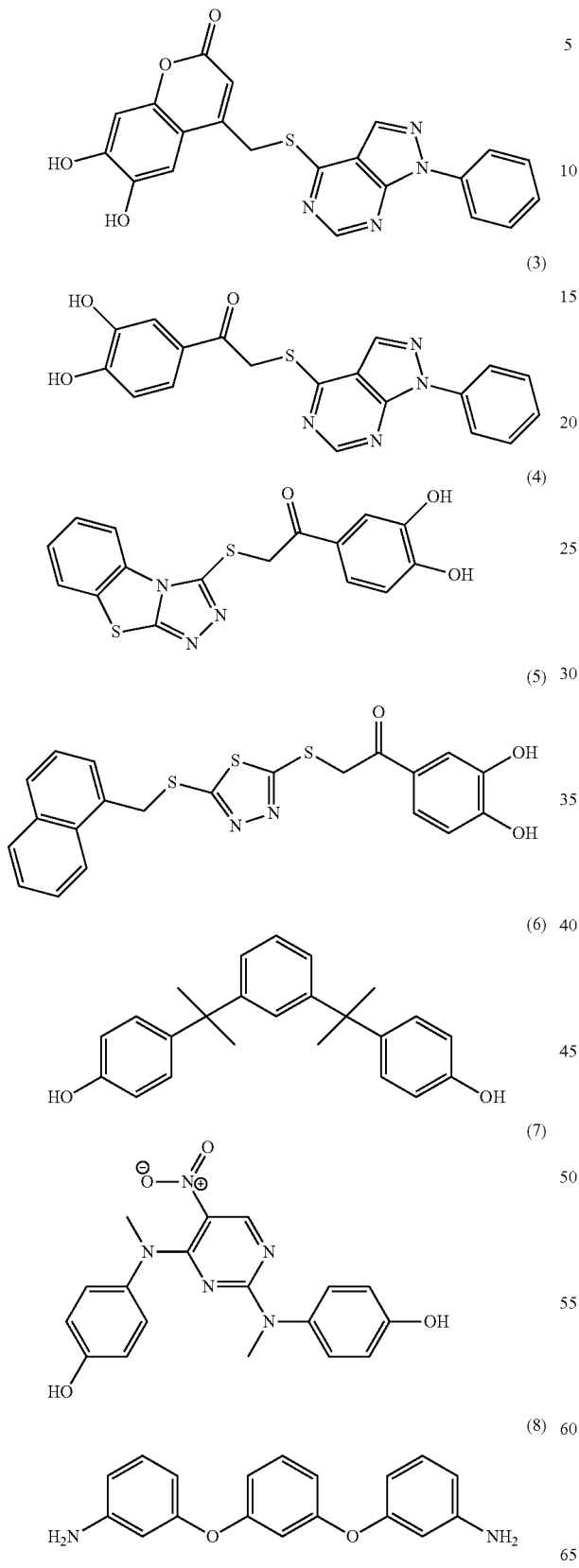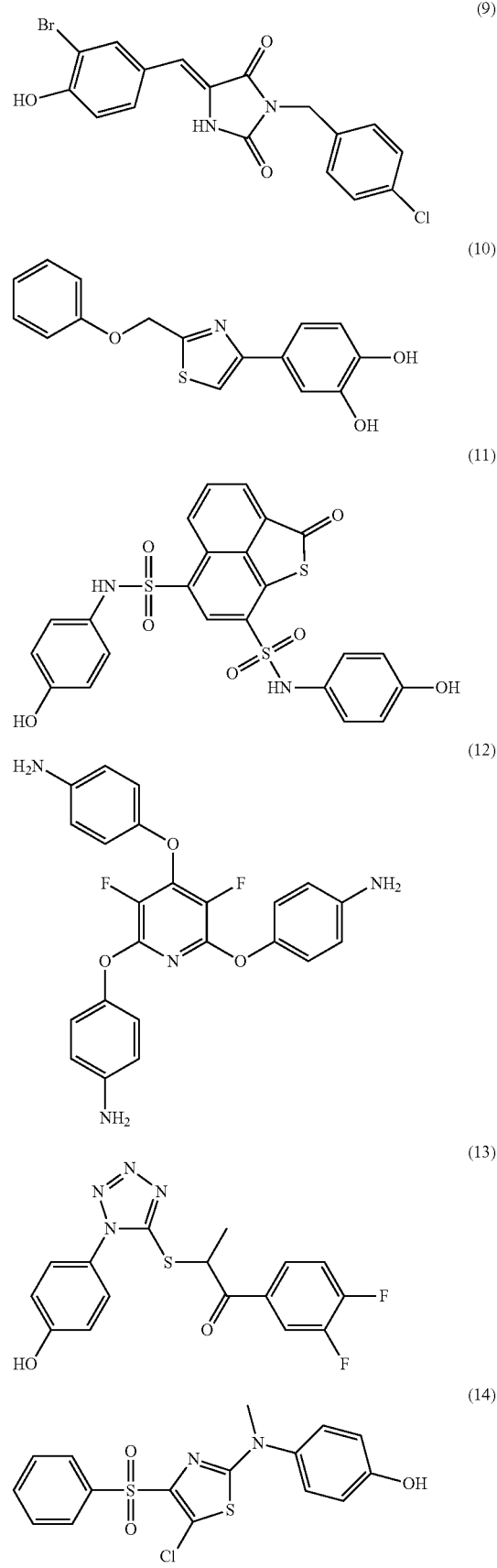

-continued (15)

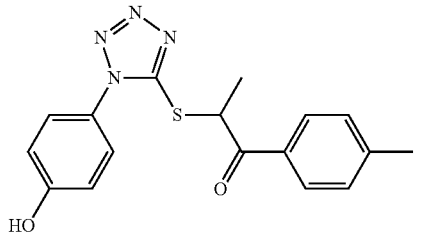

(16)

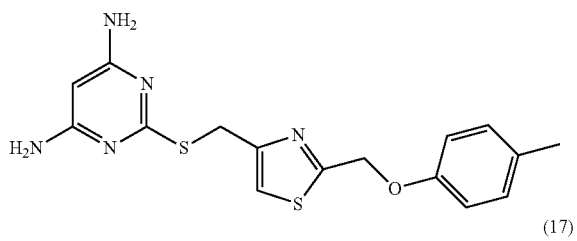

(17)

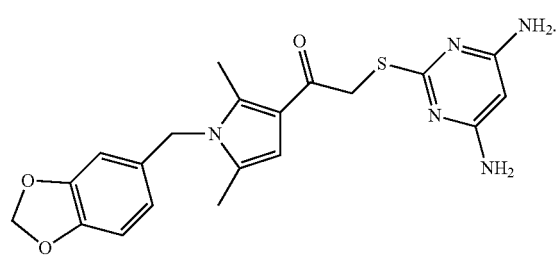

5. The method according to claim 1, wherein the IgG-Fc or Fc fusion protein is an immunoglobulin or a fragment of an immunoglobulin.

6. The method according claim 1, wherein the IgG-Fc or Fc fusion protein is a monoclonal antibody.

7. The method according to claim 1, wherein the IgG-Fc or Fc fusion protein is contained in a cell culture medium.

8. An affinity separation matrix, wherein the low-molecular-weight compound represented by the general formula (I):

ArX-(Linker)-ArYHB   (1)

wherein
ArX is a structure containing an optionally substituted aromatic six-membered ring,
ArYHB is a structure containing an optionally substituted aromatic six-membered ring having a proton donor, the atom group "Linker" is a structure containing optionally substituted tetrazole, optionally substituted hydantoin, optionally substituted pyrrol, optionally substituted pyridine, optionally substituted 1,3,4-thiadiazole, optionally substituted triazole, optionally substituted aminopyrazolo[3,4-d]pyrimidine, optionally substituted thiazole or nitropyrimidine, or is represented by —U—CZ—V—, wherein CZ is a structure containing an optionally substituted benzene ring or an optionally substituted naphthalene ring, and U and V are respectively composed of a non-hydrogen atom not containing a ring structure and binds ArX with ArYHB, with the proteinaceous substance, is immobilized on a water-insoluble base material through a spacer binding to the "Linker" of the low-molecular-weight compound.

9. The method according to claim 2, wherein the ArX in the low-molecular-weight compound has any one of a halogen group, an amino group, a hydroxy group or a methyl group as a substituent, or the Arx has a structure containing any one of a benzene ring, a naphthalene ring or 1,2-methylenedioxybenzene, or the Arx has both of the substituent and the structure.

10. The method according to claim 9, wherein the IgG-Fc or Fc fusion protein is an immunoglobulin or a fragment of an immunoglobulin.

11. The method according to claim 2, wherein the IgG-Fc or Fc fusion protein is an immunoglobulin or a fragment of an immunoglobulin.

12. The method according to claim 3, wherein the IgG-Fc or Fc fusion protein is an immunoglobulin or a fragment of an immunoglobulin.

13. The method according to claim 4, wherein the IgG-Fc or Fc fusion protein is an immunoglobulin or a fragment of an immunoglobulin.

14. The method according claim 9, wherein the IgG-Fc or Fc fusion protein is a monoclonal antibody.

15. The method according to claim 2, wherein the IgG-Fc or Fc fusion protein is a monoclonal antibody.

16. The method according to claim 3, wherein the IgG-Fc or Fc fusion protein is a monoclonal antibody.

17. The method according to claim 4, wherein the IgG-Fc or Fc fusion protein is a monoclonal antibody.

18. The method according to claim 2, wherein the IgG-Fc or Fc fusion protein is contained in a cell culture medium.

19. The method according to claim 3, wherein the IgG-Fc or Fc fusion protein is contained in a cell culture medium.

20. The method according to claim 4, wherein the IgG-Fc or Fc fusion protein is contained in a cell culture medium.

* * * * *